(12) United States Patent
Eggli

(10) Patent No.: US 8,808,374 B2
(45) Date of Patent: Aug. 19, 2014

(54) DEVICE FOR IMPLANTING A SYSTEM FOR LOADING A CRUCIATE LIGAMENT IN A KNEE JOINT

(75) Inventor: Stefan Eggli, Bern (CH)

(73) Assignee: Mathys AG Bettlach, Bettlach (CH)

( * ) Notice: Subject to any disclaimer, the term of this patent is extended or adjusted under 35 U.S.C. 154(b) by 260 days.

(21) Appl. No.: 12/810,812

(22) PCT Filed: Sep. 19, 2008

(86) PCT No.: PCT/EP2008/007903
§ 371 (c)(1),
(2), (4) Date: Sep. 29, 2010

(87) PCT Pub. No.: WO2009/083047
PCT Pub. Date: Jul. 9, 2009

(65) Prior Publication Data
US 2011/0046733 A1 Feb. 24, 2011

(30) Foreign Application Priority Data

Dec. 27, 2007 (DE) .......................... 10 2007 062 749
Apr. 1, 2008 (DE) .......................... 10 2008 016 607

(51) Int. Cl.
*A61F 2/08* (2006.01)
*A61B 17/04* (2006.01)

(52) U.S. Cl.
USPC ....................................... 623/13.14; 606/232

(58) Field of Classification Search
USPC ............... 623/13.11–13.2; 606/232, 228, 300
See application file for complete search history.

(56) References Cited

U.S. PATENT DOCUMENTS

| 4,467,478 A |   | 8/1984 | Jurgutis |
|---|---|---|---|
| 4,744,793 A | * | 5/1988 | Parr et al. ................... 623/13.14 |
| 4,828,562 A | * | 5/1989 | Kenna ......................... 623/13.13 |
| 5,458,601 A |   | 10/1995 | Young, Jr. |
| 5,507,812 A | * | 4/1996 | Moore ........................ 623/13.13 |
| 5,702,422 A |   | 12/1997 | Stone |
| 6,036,694 A | * | 3/2000 | Goble et al. .................. 606/304 |
| 6,190,411 B1 | * | 2/2001 | Lo ............................... 623/13.13 |
| 7,875,058 B2 | * | 1/2011 | Holmes, Jr. .................. 606/232 |
| 8,110,001 B2 | * | 2/2012 | Carter et al. ............... 623/13.14 |

(Continued)

FOREIGN PATENT DOCUMENTS

| DE | 3803208 A1 | 10/1989 |
|---|---|---|
| DE | 8914308 U1 | 3/1990 |

(Continued)

OTHER PUBLICATIONS

International Search report, mailed Dec. 19, 2008, issued in corresponding International Application No. PCT/EP2008/007903, filed Sep. 19, 2008.

(Continued)

*Primary Examiner* — Alvin Stewart
(74) *Attorney, Agent, or Firm* — Christensen O'Connor Johnson Kindness PLLC

(57) ABSTRACT

A device for implantation in a bone is disclosed, wherein this device is a component part of a system, for controlled loading of the reconstructure anterior crucual ligament (ACL) of a knee joint. The device may comprise an outer body, which is provided with a damping mechanism between a distal end and a proximal end. Arranged inside the damping mechanism there is at least one securing element for fixing at least one thread which, at the proximal end of the device, is guided out from the outer body through an aperture in the base.

24 Claims, 6 Drawing Sheets

(56) References Cited

U.S. PATENT DOCUMENTS

| | | | |
|---|---|---|---|
| 8,663,325 B2 * | 3/2014 | Graf et al. | 623/13.14 |
| 2002/0120349 A1 * | 8/2002 | Phillips | 623/35 |
| 2004/0098050 A1 | 5/2004 | Foerster | |
| 2005/0222488 A1 | 10/2005 | Chang | |
| 2006/0271105 A1 | 11/2006 | Foerster et al. | |

FOREIGN PATENT DOCUMENTS

| | | |
|---|---|---|
| EP | 0904033 B1 | 9/2002 |
| GB | 2 078 528 A | 6/1981 |
| JP | 2000-507469 A | 6/2000 |
| WO | 00/13601 A1 | 3/2000 |
| WO | 02/38059 A2 | 5/2002 |

OTHER PUBLICATIONS

Office Action, dated Feb. 25, 2011, issued in corresponding German Application No. 10 2008 016 607.3, filed Apr. 1, 2008, 5 pages.

* cited by examiner

DEVICE FOR IMPLANTING A SYSTEM FOR LOADING A CRUCIATE LIGAMENT IN A KNEE JOINT

The invention relates to a device for implantation in a bone and to a system for controlled loading of a reconstructed anterior cruciate ligament, wherein the device for implantation according to the invention is integrated within the system according to the invention.

The human knee joint is stabilised within the interior cavity of the knee joint by the anterior cruciate ligament and the posterior cruciate ligament. In the case of a twisting trauma of the knee joint, these ligaments are very often overstretched until a rupture or tear occurs. In this context, the anterior cruciate ligament is affected approximately 9-times more frequently than the posterior cruciate ligament. All attempts at conservative therapy or experiments with stitching the anterior cruciate ligament are associated with considerable problems. Accordingly, in the case of a persistent instability of the injured knee joint, the anterior cruciate ligament is removed according to the prior art, and the stability of the knee joint is restored using a transplant made of tendon material, either of patellar tendon, semitendinous tendon or quadriceps tendon. One disadvantage of this method is that the latter ligament structure is avital, that is to say, it no longer provides any sensitivity and begins to lose stability again over time.

The published German patent specification DE 38 03 208 A1 describes a device for reconstruction surgery, wherein the anterior cruciate ligament in the human knee joint is permanently restored. In this context, the tibia bone is stabilised relative to the femur and a full range of movement is restored to the knee by inserting a replacement ligament within the knee joint through precise local attachment of the ends and of the angular position in such a manner that, in the event of a movement of the knee joint, the replacement ligament experiences no change in length (isometric movement) or that the change in length of the replacement ligament corresponds to the physiometric movement of a natural ligament. The disadvantage with this device is that the anterior cruciate ligament in the human knee joint is permanently restored by a replacement ligament, which also comprises a transplant. Accordingly, the injured, natural ligament is permanently removed from the knee joint, and the artificial, replacement ligament takes over its function only inadequately.

The U.S. Pat. No. 5,702,422 describes a method for the repair of tearing and ruptures of an anterior cruciate ligament of a human knee, wherein the ligament is reconnected to its anatomical insertion in the gap between the two condyles of the femur bone by means of a pin for the wound suture. In this context, the healing of the insertion is accelerated by forming a recess in the spongiosa for the collection of blood.

The disadvantage of this method is that the wound suture is connected to the pin, so that a tension is permanently applied to the torn or ruptured ligament, and the healing ligament is longer than the original, healthy ligament and is accordingly impaired in its functionality.

The invention is based upon the object of providing a device and a system for a temporary relief of a reconstructed, natural anterior cruciate ligament in the human knee joint or for any required ligament structure of a human or animal joint.

With regard to the device and the system, the named object is achieved according to the invention by the features of claim 1 and claim 17 respectively. Advantageous further developments form the subject matter of the dependent claims referring back to these claims.

The device according to the invention for implantation into a bone therefore comprises an outer body provided with an external screw-thread, which provides a front end and a base. Within its interior, between a distal end and a proximal end, the outer body provides a damping device, wherein at least one fixing element is arranged within the damping device, which fixes at least one thread, which is guided out of the outer body at the proximal end of the device through a recess in the base.

The invention is based upon the concept that every ligament in the human body provides a largely self-healing tendency. Accordingly, at present, fibulotalar ligament ruptures or AC joint ruptures are practically all treated conservatively. Even a rupture of the large Achilles tendon is nowadays treated conservatively in many centres. As already mentioned, conservative treatment of the anterior cruciate ligament has failed in the past. In fact, scarring of the ligament did occur, but the instability of the knee joint persisted. The stabilising effect of this ligament is lost, because a knee joint cannot be immobilised for the healing of the ligament structure. The anterior cruciate ligament requires approximately six weeks for primary healing. Immobilisation for this duration is absolutely impossible, because the knee joint would become rigid for practical purposes as a result of an immobilisation of this kind. However, if the knee joint is moved during the healing phase with persistent instability, an antero-posterior translation of the knee joint of up to 10 millimeters occurs with every increasing flexion. This translational instability is, so to speak, built-in with the self-healing of the ligament. The ligament cannot heal back to the original length, but is lengthened and therefore no longer fulfils the stabilising function.

The advantages achieved with the device according to the invention for implantation in a bone comprise, in particular, the stabilisation of the knee joint during the self-healing phase in every flexional position with exactly the correct antero-posterior translation. In a sense, during the healing phase, the device according to the invention, which is conceived as an isotonic knee-joint screw and which is an integral component of the system according to the invention, takes over the joint stabilisation, which was formerly provided by the natural, or endogenous and healthy ligament. By means of the isotonic knee-joint screw and respectively the system according to the invention with the device according to the invention, the lower leg is permanently drawn into a posterior drawer position relative to the thigh.

Accordingly, the two ruptured bundles of fibres of the anterior cruciate ligaments are drawn towards one another over a shortest possible distance. With the help of the system according to the invention, the two ligament stumps can advantageously heal together again in the original position without the loss of stability and with the original length, and, in particular, can therefore once again completely fulfil their original function, the stabilisation of the joint.

Furthermore, it is advantageous if the damping device is fitted with a spiral spring, to which a variable pressure can be applied, which can be adjusted in a controlled manner by the operator by means of a tool connected to a force sensing device. The fact that the spiral spring in the device according to the invention is arranged on the base of the outer housing, which is formed in a cylindrical shape, advantageously achieves a good mechanical stability in the event of an application of medium to high compressive forces during the implantation.

Furthermore, it is advantageous if the damping device provides an axially displaceable clamping sleeve within the outer body, which moves in the proximal direction in the case of knee bending and knee stretching movements and in this context once again compresses the spring so that the knee movements are dampened.

Moreover, it is advantageous if the spiral spring encloses the proximal end of the clamping sleeve and is disposed in contact with the flange of the clamping sleeve. Accordingly, a translational movement of the spiral spring within the interior of the outer body is prevented, since both ends of the spiral spring are mounted on a structurally stable surface.

Moreover, it is advantageous if the flange is provided with an internal screw-thread. As a result of the surface structure of the internal screw-thread, the thread clamped primarily within the flange is subjected to an additional holding.

Furthermore, it is advantageous if the fixing element of the device according to the invention is designed as a cone. This guarantees that the cone with the wound thread is also accommodated without material stresses within the clamping sleeve, especially within the transitional region towards its flange.

The cone is expediently attached with its distal end to a screw extension of a screw, wherein the screw is to be screwed with its external screw-thread into the internal screw-thread of the clamping sleeve, so that the thread can advantageously be wound onto the cone in a controlled manner and can, at the same time, be clamped. Moreover, the advantage is also achieved that the force, with which the screw is screwed in, is disposed in a defined relationship to the clamping force on the thread, wherein this relationship is naturally known to the user or respectively the operator.

According to an advantageous development, the screw head of the screw provides a recess, which is formed in the shape of a polygon or respectively a hexagon, thereby preventing a slipping of the tool during the application of a tensile force.

In an expedient further development, the thread of the device according to the invention comprises an elastic material, thereby allowing a uniform tensile stress and preventing a tearing of the thread. In order to reinforce these properties, an additional element is provided in one exemplary embodiment at the distal end of the elastic thread, wherein this elastic body preferably comprises a polymer or an elastomer. An elastic material for the thread or respectively the body is also advantageous, because the tensile forces on the reconstructed anterior cruciate ligament are relieved and compensated as a result.

The system according to the invention for a controlled stressing or loading of the reconstructed anterior cruciate ligament during the healing phase advantageously comprises the device according to the invention (isotonic knee-joint screw) for implantation in a bone, comprising at least one thread, which is provided as a temporary replacement for the reconstructed anterior cruciate ligament, and a holding element for the at least one thread, with which the tension in the thread is built up.

It is advantageous if the knee-joint screw is inserted into a distal bone of a joint, so that the direction of the applied tensile force or respectively tensile stress extends away from the joint. Accordingly, the healing, endogenous anterior cruciate ligament is also advantageously relieved.

Moreover, it is advantageous, if the system according to the invention is based on the device being screwed into the bone at an acute angle relative to the surface of the bone, thereby guaranteeing its stable anchoring, which is not destabilised by a loading with tensile forces. The direction of the acute angle within the bone corresponds largely to the course of the anterior cruciate ligament in the interior of the knee joint.

Moreover, it is advantageous that, after a fitting of the system according to the invention, the knee joint remains fixed during the healing phase in the posterior drawer position, and any impacts occurring during daily mobilisation exercises or uncontrolled movements during sleep are taken up by the spiral spring.

A further advantage is that the operative intervention for the fitting of the system according to the invention is implemented in a minimally invasive manner and only two conventional arthroscopic incisions are required for this purpose.

Furthermore, it is advantageous that the endogenous ligament remains preserved and need no longer be removed. Accordingly, proprioceptivity is also preserved, so that the ligament structure is no longer avital after the healing process. Moreover, a removal of exogenous transplant material is no longer required, so that the duration of the operative intervention is advantageously practically halved and the probability of a complication is significantly reduced. Accordingly, once again, the hospitalisation of the patient provided with the system according to the invention is also significantly shortened.

Exemplary embodiments of the present invention are described in the following section. The structure and the use of the invention and its advantages and objects are best understood with reference to the following description in conjunction with the associated drawings. The drawings are as follows.

Components corresponding to one another are provided with the same reference numbers in all of the drawings.

Figure 1:
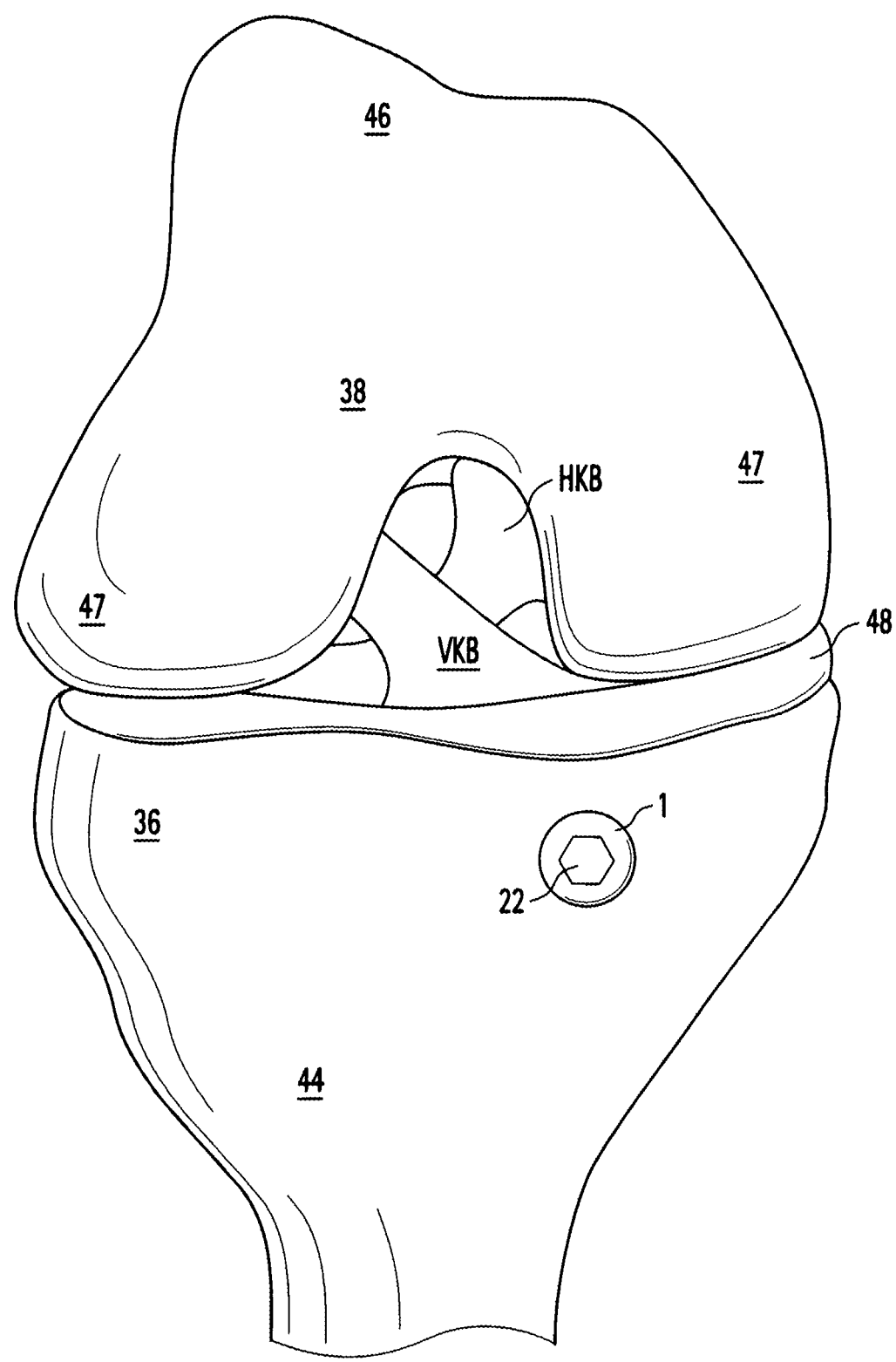
FIG. 1 shows an anterior view of a human knee in the flexed position with a first exemplary embodiment of the device according to the invention.

FIG. 1 shows an anterior view of a human knee joint in the flexed position with a first exemplary embodiment of the device 1 according to the invention for implantation in a bone, wherein this exemplary embodiment of the device 1 according to the invention comprises a cylindrical outer body 3 provided with an external screw-thread 2 with a front end 4 and a base 5. Within its interior 6, the cylindrical outer body 3 is provided between its distal end 8 and its proximal end 9 with a damping device 7, wherein, within the damping device 7, at least one fixing element 10 is arranged, which fixes at least one thread 11, which is guided at the proximal end 9 of the device 1 through a recess 12 in the base 5 out of the cylindrical outer body 3, which is clearly evident in FIG. 7.

The device 1 according to the invention can be screwed into a bone at an acute angle α, relative to a tangent to a bone surface into a borehole, which extends in the distal-proximal direction. The acute angle α is disposed within the range from 40° to 50°, but is preferably 45°. This first exemplary embodiment shows a human knee joint, wherein the device 1 according to the invention is screwed into a borehole in the proximal end of a tibia bone 44. The position 45 of the borehole is disposed below the anterior cruciate ligament insertion in a lateral-anterior direction.

Figure 2:
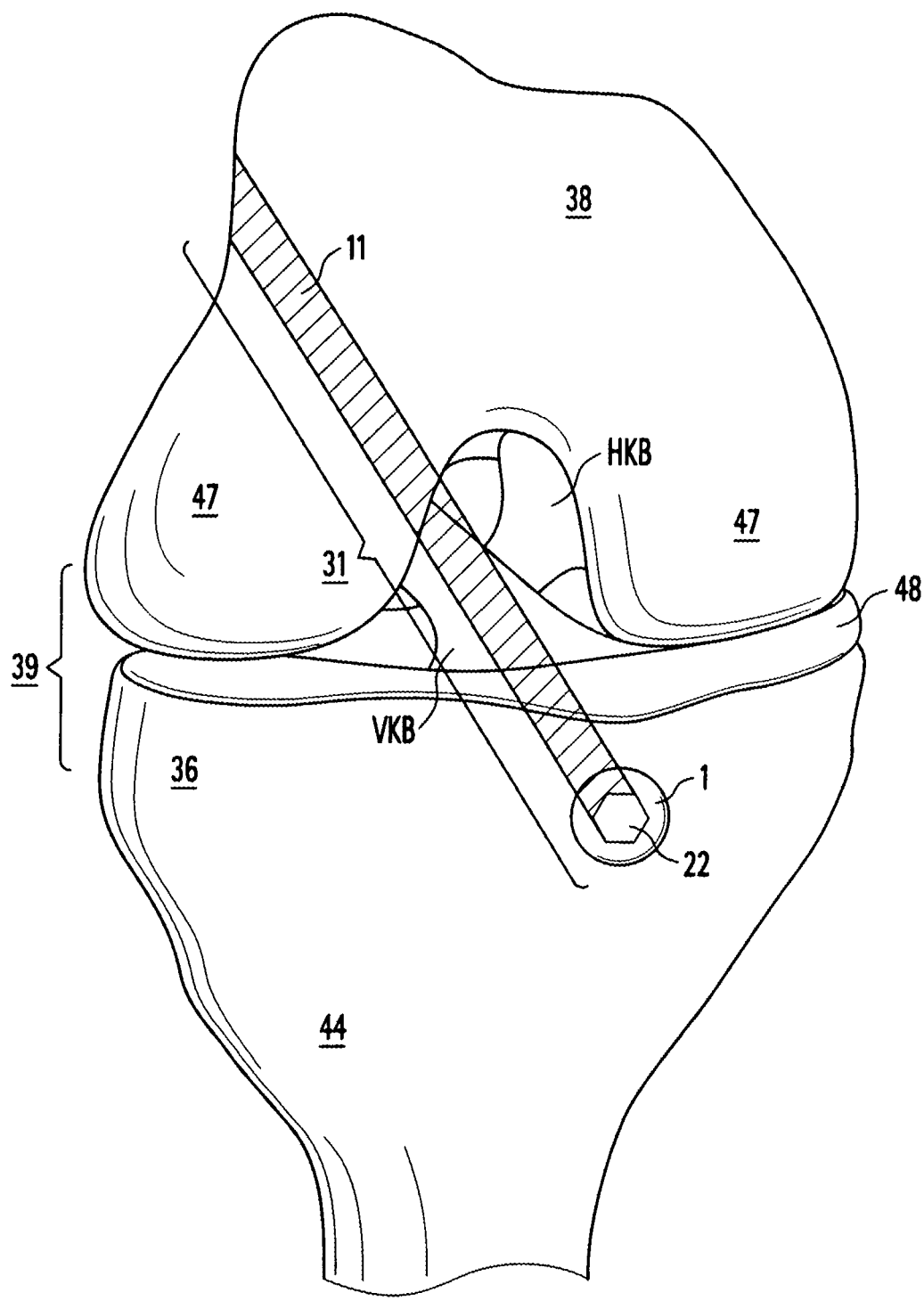
FIG. 2 shows an anterior view of a human knee in the flexed position with a first exemplary embodiment of the system according to the invention for a controlled loading of an anterior cruciate ligament.

FIG. 2 shows an anterior view of a human knee joint in the flexed position with an exemplary embodiment of the system according to the invention for a controlled stressing or loading of an anterior cruciate ligament ACL. The system 31 according to the invention for a controlled stressing or loading of the anterior cruciate ligament ACL reconstructed, for example, by stitching, comprises a device 1 for implantation into a bone, at least one thread 11 as a replacement for the reconstructed anterior cruciate ligament ACL and a holding element 32 for the at least one thread 11, and is preferably applied during the healing phase of a ruptured and reconstructed ligament for its relief.

Figure 3A:
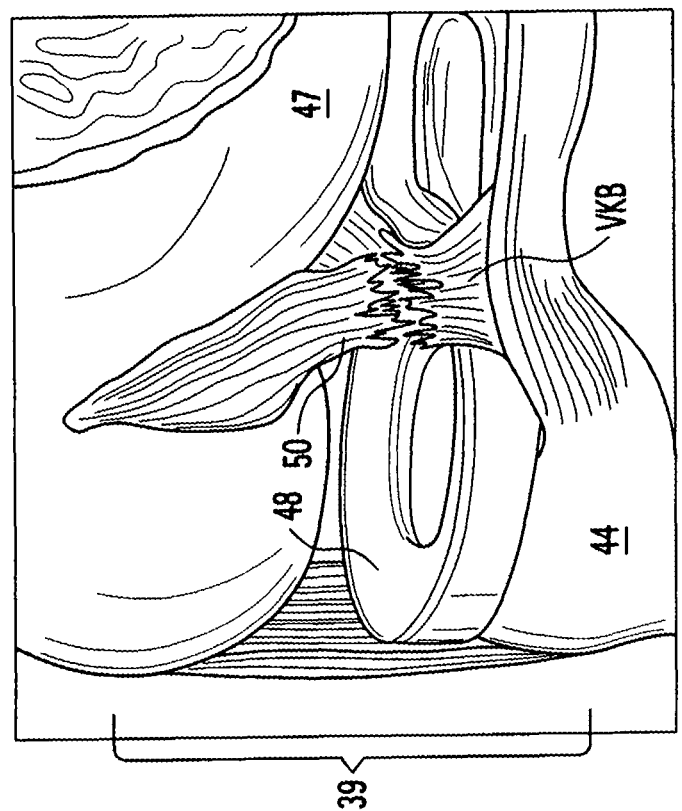
FIG. 3a shows an enlargement of the detail indicated in FIG. 3.
Figure 3:
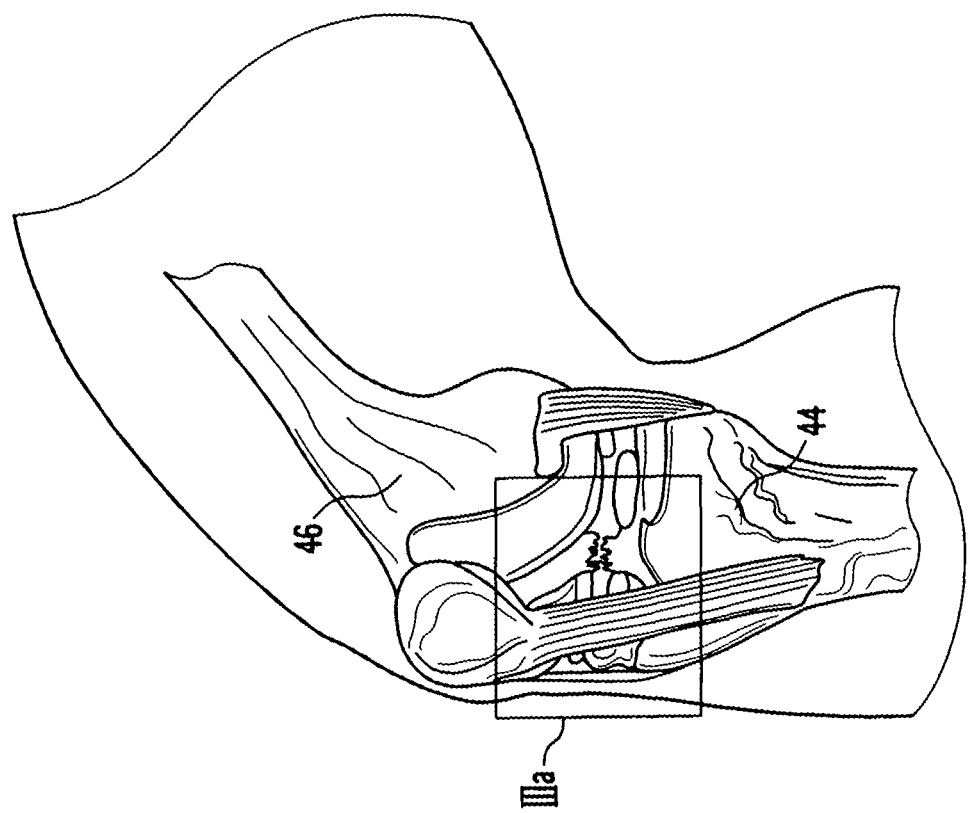
FIG. 3 shows a flexed human knee, for which a use of the device according to the invention and the system according to the invention is meaningful.

FIG. 3 illustrates a flexed human knee, for which a use of the device according to the invention and of the system according to the invention is preferably provided.

FIG. 3a shows an enlargement of the detail indicated in FIG. 3 with an anterior cruciate ligament rupture 50. The ruptured anterior cruciate ligament ACL is reconstructed using appropriate means, wherein, during the subsequent healing phase, the reconstructed anterior cruciate ligament ACL may be stressed only very slightly, so that the ruptured anterior cruciate ligament ACL grows together again in such a manner that it can subsequently fulfil its function completely. Because the system 31 according to the invention providing a device 1 with a damping device 7, comprising a thread 11 and a holding element 32, is used in the injury shown in FIG. 3, the reconstructed anterior cruciate ligament ACL is not stressed even by small movements, since, especially through the at least one thread 11, which is stretched from the tibia to the femur with a defined force of approximately 120 newtons, optimised by the operator, the system 31 according to the invention completely takes over the function of the healing anterior cruciate ligament ACL.

The device 1 according to the invention is implanted into a bone 36 at a distal side of a joint. In the case shown in FIGS. 3 and respectively 3a, it is the proximal end of a tibia bone 44, which adjoins the human knee joint or respectively its joint gap 39.

A variable tensile stress can be applied, via the device 1 according to the invention, which is a component of the system 31 also according to the invention, to the at least one thread 11, which takes over the function of the anterior cruciate ligament ACL to be relieved during the healing process, so that, during an implementation of the system 31 according to the invention, the operator can adapt the tensile stress in an optimal manner after the reconstruction of the anterior cruciate ligament ACL or respectively after the reconstruction of a ligament in general. This guarantees that the system 31 according to the invention takes over the function of the reconstructed ligament or respectively the function of the reconstructed anterior cruciate ligament ACL during its healing phase.

Figure 4:
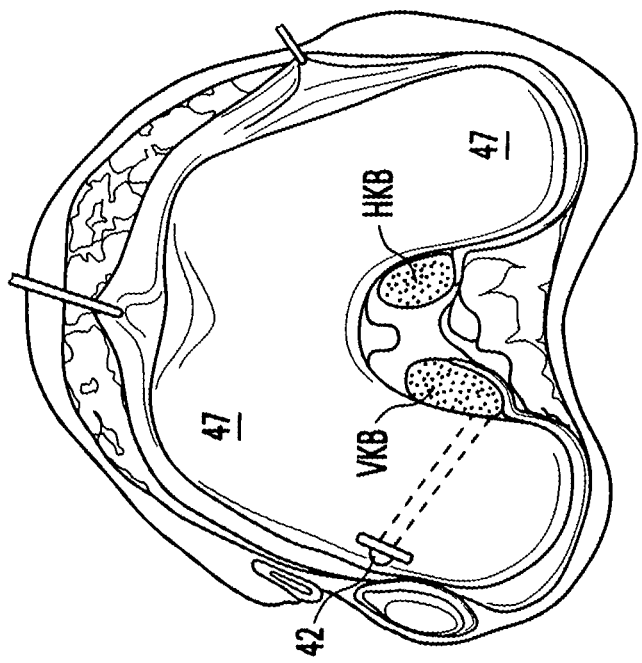
FIG. 4 shows a sectional view of the distal end of a femur bone in the flexed position with the anterior cruciate ligament and the posterior cruciate ligament and the course of at least one thread of the system according to the invention within the medial (internal) condyle.

FIG. 4 shows a sectional view of the distal end of a femur bone 46 or respectively a sectional view of both condyles 47 of the human knee joint in the flexed position. The anterior cruciate ligament ACL and the posterior cruciate ligament PCL grow on the inside of the two condyles 47. Furthermore, the system 31 according to the invention with the holding element 32 and the at least one thread 11 is illustrated schematically in FIG. 4, wherein the holding element 32 and the thread 11, which is indicated by a dotted line, are projected into the plane of the drawing. Within the human knee joint, the at least one thread 11 extends through a first bone tunnel 35 within the tibia bone 44 via the joint gap 39 into a second bone tunnel 37 within a condyle 47, wherein the outlet opening of the second bone tunnel 37 is disposed laterally or respectively on the outside of this condyle 47, and the at least one thread 11 is stretched largely parallel to the reconstructed anterior cruciate ligament ACL.

Figure 5:
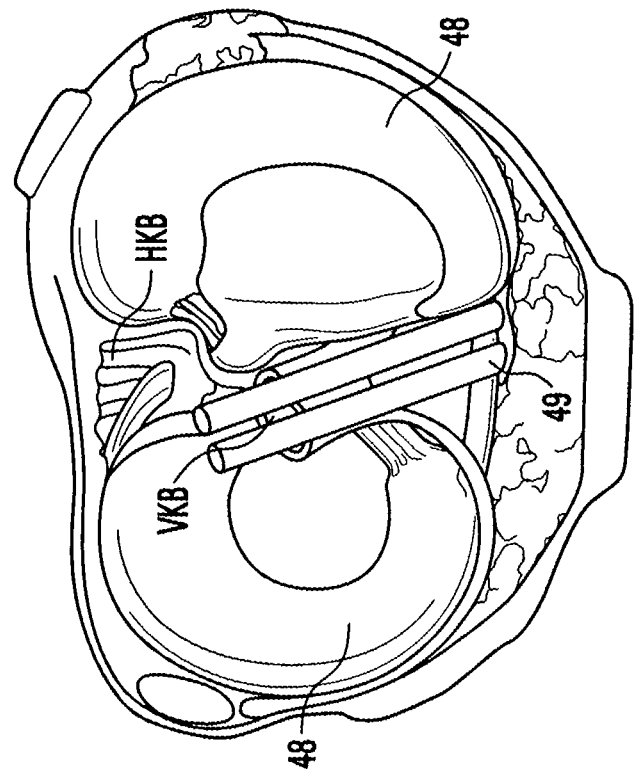
FIG. 5 shows a plan view of a knee-joint gap with the two meniscuses and the anterior cruciate ligament and the posterior cruciate ligament.

FIG. 5 shows a sectional plan view of a knee-joint gap 39 with the two meniscuses 48 and with the anterior cruciate ligament ACL and the posterior cruciate ligament PCL viewed from proximal or respectively from above. With this exemplary embodiment of the invention, a double thread 49 extends parallel to the anterior cruciate ligament ACL for the relief of the reconstructed anterior cruciate ligament ACL disposed beneath it.

Figure 6:
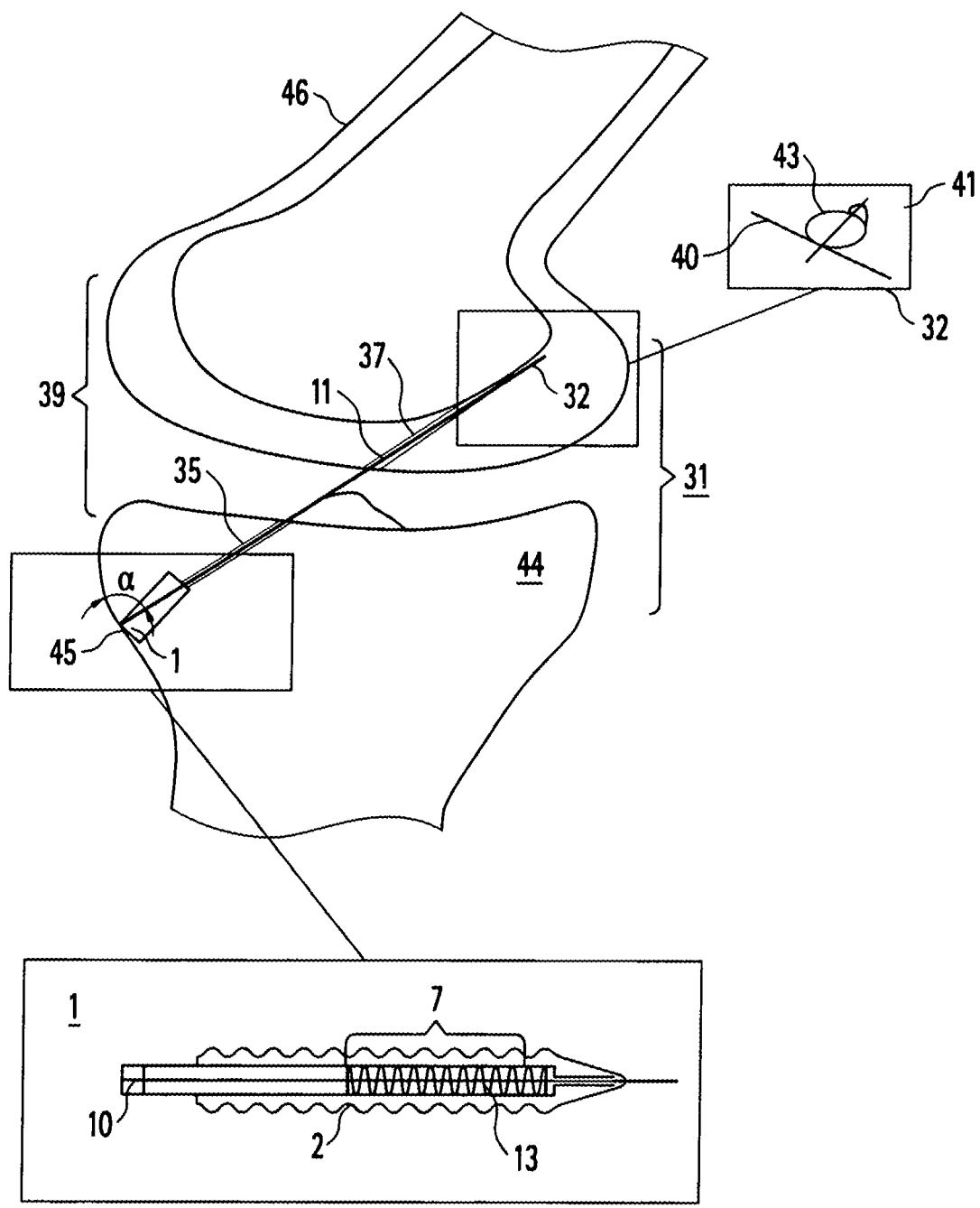
FIG. 6 shows a schematic section disposed parallel to the sagittal plane through a human knee joint, in which the system according to the invention is used.

FIG. 6 shows a schematic section through a human knee joint, disposed parallel to the sagittal plane and held in an isotonic manner in an anterior drawer position, on which the system with 31 according to the invention, which comprises a holding element 32, at least one thread 11 and the device 1 according to the invention, is used. In this exemplary embodiment, the system 31 according to the invention comprises the device 1 already described for implantation in a bone, preferably in the proximal end of a human tibia bone 44, providing at least one thread 11 as a functional replacement or respectively support for the reconstructed ligament or respectively the anterior cruciate ligament ACL of a human knee joint and providing a holding element 32, which attaches the at least one thread 11 to a surface of a proximal bone of a joint, especially of a knee joint during the healing phase of the reconstructed ligament. FIG. 6 shows that the at least one thread 11 extends within a first bone tunnel 35 in a distal bone 36 of a joint, especially of a knee joint, and within a second bone tunnel 37 within a proximal bone 38 of the joint or respectively of the knee joint, wherein the thread 11 or respectively several threads 49 arranged parallel to one another are stretched across the joint gap or respectively across the knee-joint gap 39. The at least one thread 11 emerges from the second bone tunnel 38 and is fixed by means of the holding element 32 at a proximal end outside the second bone tunnel 37. The holding element comprises a metal plate 40 and a stopper 41 and is disposed at the proximal end of the second bone tunnel 37, wherein the stopper 41 which is formed as a knot 42 in the thread 11 or respectively as a common knot of all threads 49, fixes the thread 11 or respectively the threads 49 to the metal plate 40. The stopper 41 can also be formed as a bead 43, wherein the end of the at least one thread 11 is welded to the bead 43 and the bead 43 itself is manufactured from a bio-compatible material.

Figure 7:
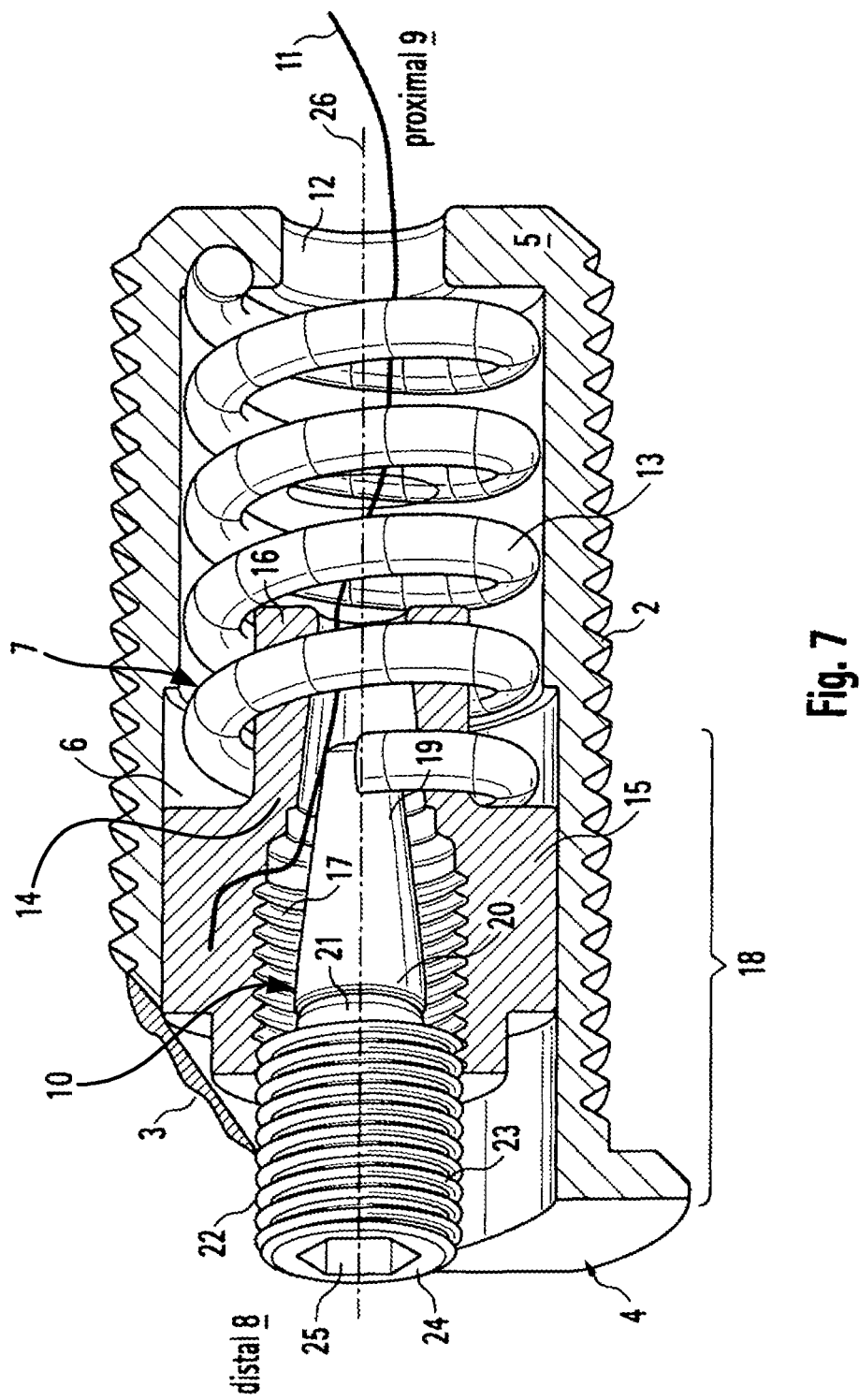
FIG. 7 shows a sectional view of the device according to the invention for implantation in a bone.

FIG. 7 shows a sectional view of the device 1 according to the invention for implantation in a bone. The device 1 according to the invention comprises a cylindrical outer body 3, which is provided with an external screw-thread 2, in order to be screwed into a bone 44 or respectively into bone tissue. In this manner, the cylindrical outer body anchors itself in the bone tissue, in that the latter grows well especially at the surface of its external screw-thread. The cylindrical outer body 3 provides a front end 4 and a base 5, wherein, after the introduction of the device 1 according to the invention into the bone, the front end 4 is orientated towards the bone surface. In the interior 6 of the device 1 according to the invention or respectively of the cylindrical outer body 3, a damping device 7 is disposed between a distal end 8 and a proximal end 9, wherein the damping device 7 provides at least one fixing element 10, which is preferably designed as a cone 19 and, at the distal end 8, fixes at least one thread 11, which extends largely within a damping device 7, parallel to its longitudinal axis 26 and is guided out of the cylindrical outer body 3 through a recess 12 in the base 5 at the proximal end 9 of the device 1.

The damping device 7 is fitted with a spiral spring 13, to which a pressure adjustable by an operator is applied, and is in contact at its proximal end 9 with the base 5 of the cylindrical outer body 3. Furthermore, within the damping device 7, a sleeve or respectively a clamping sleeve 14 is disposed, which provides a flange 15 with an internal screw-thread 17, with which the spiral spring 13 is in contact with its distal end 8. The proximal end 16 of the sleeve 14 is inserted into the spiral spring 13, so that the latter encloses the sleeve 14 in the region of the distal half 18 of the cylindrical outer body 3. The fixing element 10 or respectively the cone 19 is attached with its distal end 20 to a screw extension 21 of a screw 22, wherein the screw 22 is provided for a controlled winding of the thread 11 onto the cone 19, thereby increasing the tension of the thread. In this context, the screw 22, of which the screw head 24 provides a recess 25 in the shape of a polygon, preferably a hexagon, is screwed with its external screw-thread 23 into the internal screw-thread 17 of the flange 15.

A further exemplary embodiment of the device 1 according to the invention is realised by providing the damping device 7 with a thread 11 made of an elastic material, wherein the thread is attached by clamping to the at least one fixing element 10. The clamping of the elastic thread 11 is realised by winding the latter onto the cone 19 and accordingly clamping it to the internal wall at the proximal end 16 of the clamping sleeve 14 and the cone 19.

An additional exemplary embodiment of the present invention is provided by a device 1 according to the invention with a damping device 7 and an elastic thread 11, at the distal end of which an elastic body comprising a polymer or an elastomer encloses the at least one thread or several threads. However, the two last named exemplary embodiments are not illustrated in drawings.

The invention is not restricted to the exemplary embodiment presented in the drawings, especially not to a use for a knee joint. A use of the invention as a temporary functional replacement for a shoulder joint or another joint is also possible. All of the features described above and presented in the drawings can be combined with one another as required.

The invention claimed is:

1. A device for implantation into a bone, comprising:
   an outer body provided with an external screw-thread, with a front end and a base;
   a damping device disposed in the interior of the outer body between a distal end and a proximal end, wherein the damping device includes an axially displaceable clamping sleeve disposed within the outer body and a spiral spring, wherein a proximal end of the clamping sleeve is inserted into the spiral spring;
   at least one fixing element disposed within the damping device, the at least one fixing element configured to fix at least one thread, which is guided out of the outer body at the proximal end of the device through a recess in the base, wherein the thread is clamped to the at least one fixing element,
   wherein the fixing element is configured as a cone for accommodation within at least the proximal end of the clamping sleeve, the cone being attached at its distal end to a screw extension of a screw, and
   wherein the clamping sleeve is provided with an internal screw-thread extending from a distal end of the clamping sleeve for threading engagement with the screw over the entire length of the clamping sleeve excluding the proximal end of the clamping sleeve inserted into the spiral spring.

2. The device according to claim 1, wherein the spiral spring is in contact with the base of the outer body at its proximal end and opposes an applied variable pressure.

3. The device according to claim 2, wherein the at least one thread extends within the spiral spring, parallel to its longitudinal axis.

4. The device according to claim 1, wherein the clamping sleeve includes a flange.

5. The device according to claim 4, wherein the spiral spring is in contact with the flange.

6. The device according to claim 4, wherein the flange is provided with at least a portion of the internal screw-thread.

7. The device according to claim 6, wherein the length of the cone corresponds approximately to the length of the internal screw-thread of the flange.

8. The device according to claim 6, wherein the screw is to be screwed with its external screw-thread into the internal screw-thread of the flange of the clamping sleeve.

9. The device according to claim 8, wherein a screw head of the screw provides a recess in the form of a polygon or hexagon.

10. The device according to claim 4, wherein the clamping sleeve is arranged with its flange in the region of the distal half of the outer body.

11. The device according to claim 1, wherein an elastic body, which encloses at least one thread or several threads, is provided on the thread at its distal end.

12. The device according to claim 11, wherein the elastic body is a polymer or an elastomer.

13. The device according to claim 1, wherein the device can be screwed into a borehole in a bone at an acute angle within the range from 40° to 50° relative to a tangent to a bone surface.

14. The device according to claim 1, wherein the outer body is cylindrical in shape.

15. A system for a controlled loading of the anterior cruciate ligament (ACL) reconstructed from the two fibre bundles during the healing phase, which provides a device for implantation into a bone according to claim 1, fixes at least one thread as a replacement for the reconstructed anterior cruciate ligament (ACL), and provides a holding element for the at least one thread.

16. The system according to claim 15, wherein the device can be screwed into a borehole in a bone at an acute angle ($\alpha$) within the range from 40° to 50° relative to a tangent to a bone surface.

17. The system according to claim 15, wherein a variable tensile stress can be applied via the device to the at least one thread.

18. The system according to claim 15, wherein the at least one thread extends at one end within a first bone tunnel, wherein the first bone tunnel adjoins the borehole in the distal bone, and also extends within a second bone tunnel in a proximal bone of a joint and bridges a joint gap.

19. The system according to claim 18, wherein the at least one thread emerges from the second bone tunnel and is fixed by the holding element at a proximal end of the second bone tunnel.

20. The system according to claim 19, wherein the holding element comprises a metal plate and a stopper, wherein the metal plate is in contact with the proximal end of the second bone tunnel, and the stopper fixes the at least one thread to the metal plate.

21. The system according to claim 20, wherein the stopper is formed as a knot in the thread or as a common knot of all threads.

22. The system according to claim 21, wherein the stopper is formed as a bead, wherein one end of the at least one thread is welded or knotted to the bead.

23. The system according to claim 15, wherein the thread is configured to control the loading on the reconstructed anterior cruciate ligament (ACL).

24. The system according to claim 15, wherein the thread coexists with the reconstructed anterior cruciate ligament (ACL) during the healing phase when the device is implanted into a bone at the distal side of a joint.

* * * * *